United States Patent [19]

Tur-Kaspa et al.

[11] Patent Number: 4,910,146

[45] Date of Patent: Mar. 20, 1990

[54] AUTOMATED PLANT CULTURE PROLIFERATION SYSTEM

[75] Inventors: Yossef Tur-Kaspa, Ann Arbor, Mich.; Robert D. Hartman, Lake Placid, Fla.; Kenneth J. Hornacek, Pontiac; Kevin J. Brendel, Ann Arbor, both of Mich.

[73] Assignee: Hartmans Plants, Inc., Sebring, Fla.

[21] Appl. No.: 220,456

[22] Filed: Jul. 18, 1988

[51] Int. Cl.⁴ .............................................. C12M 3/00
[52] U.S. Cl. ................................ 435/284; 435/240.4; 47/41.01
[58] Field of Search ................ 435/284, 240.48, 240.4, 435/240.45, 240.1, 800; 47/17, 58, DIG. 1, 1 R, 1.7, 85, DIG. 3; 111/105, 104; 222/80, 83, 85

[56] References Cited

U.S. PATENT DOCUMENTS

| | | | |
|---|---|---|---|
| 3,820,480 | 6/1974 | Blackmore et al. | 111/105 X |
| 4,408,549 | 10/1983 | Quarnström | 111/105 X |
| 4,456,683 | 6/1984 | Lintihac et al. | 435/240.4 X |
| 4,481,893 | 11/1984 | Quanström | 111/105 |
| 4,616,578 | 10/1986 | Talbott | 111/105 |
| 4,827,079 | 5/1989 | Evans et al. | 435/240.4 X |

FOREIGN PATENT DOCUMENTS 132413 5/1986 European Pat. Off. .
132414 5/1986 European Pat. Off. .
6402 9/1988 World Int. Prop. O. ....... 435/240.4

*Primary Examiner*—Larry Jones
*Attorney, Agent, or Firm*—Harness, Dickey & Pierce

[57] ABSTRACT

An automated plant tissue proliferation system in which mature plants within a culture vessel are cut into a plurality of plugs using a die type cutter block. The cutter block is moved using a pick and place actuator to a work station where any extraneous nutrient media or plant material adhering to the sides of the cutter are removed using an indexed membrane sheet. A pair of opposed articulated wiping arms cause the membrane sheet to be wrapped around the cutter and pulled down vertically along its sides to remove the excess material. Thereafter, the cutter is indexed to deposit some fraction of the cut cells into a container having culture medium. Fluid pressure is used to eject material from the appropriate cells onto the media material. A number of additional containers are indexed into position with the cutter until all of the plugs of material are removed. the actuator and ejection system are so operated to distribute the plugs of plant material in a preselected array in a number of containers. The system provides rapid plant proliferation minimizing labor requirements and the liklihood of tissue culture contamination.

30 Claims, 9 Drawing Sheets

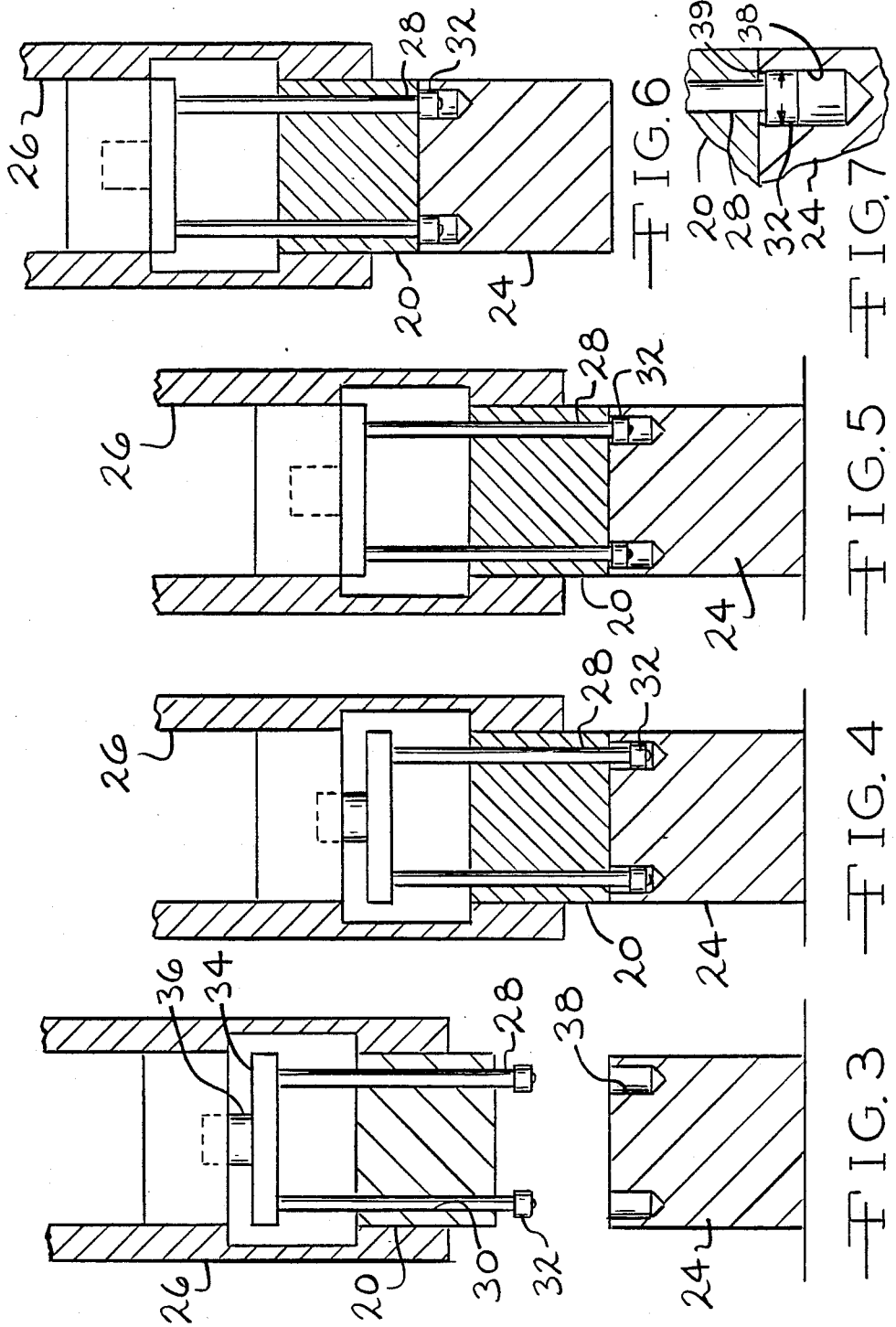

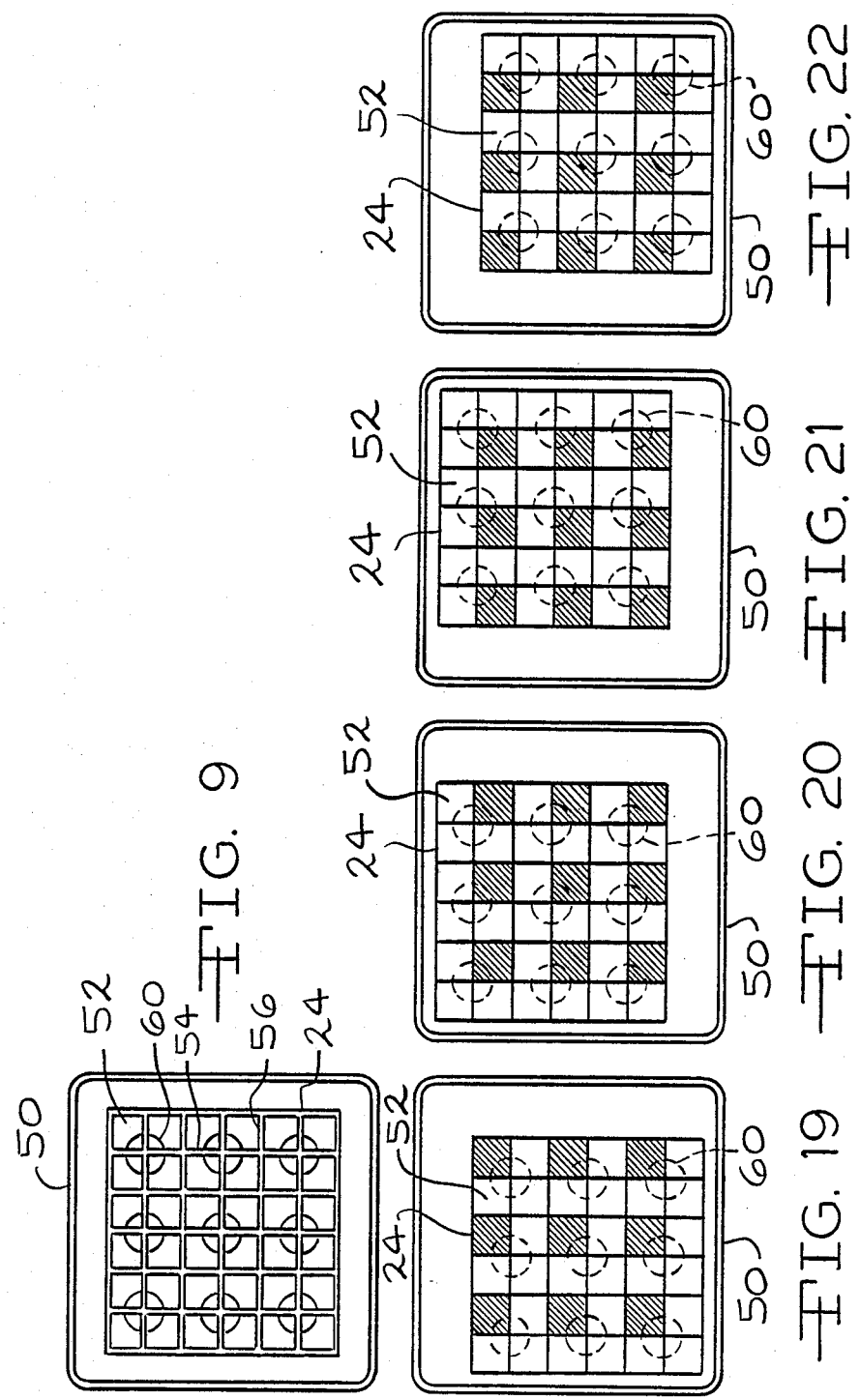

AUTOMATED PLANT CULTURE PROLIFERATION SYSTEM

BACKGROUND OF THE INVENTION

This invention relates to an automated process and device for propagation of plants using tissue culture (in vitro) techniques.

In conventional procedures for plant cloning or propagations by tissue culture, a portion of a plant is placed in a nutrient medium in an aseptic controlled environment and caused to grow. The medium typically has hormones to encourage plant growth of a desired type. Once the plant reaches a given stage of growth, it is divided and separated and placed in additional container having growth medium, thus proliferating the plant. Aseptic conditions are required to discourage bacterial and fungal contamination which can cause significant losses. The most widely used current process for aspectic plant tissue culture propagation requires an operator to manually remove plant tissue from culture medium and divide it into a number of parts which are manually aseptically replanted into containers containing new media. This procedure is slow, highly labor intensive and exposes the plant to the potential for contamination. The high labor costs associated with such processes have limited the commercial viability of this approach.

In order for in vitro proliferation systems to be commercially viable on a larger scale, an automated system is needed in which plant material is cut into uniformly sized pieces. Following the cutting process, the cut material should be distributed in a precisely controlled and uniform manner in growth vessels. Distribution of the cut plant material within the growth vessels must be uniform in order to better predict maturation time, and to more efficiently utilize the culture media required. Various systems for automated plant tissue culture proliferation systems are presently known. These systems typically employ a blender which finely divides the plant tissue into small components which are thereafter deposited on a suitable growth medium. Although these processes work well for some applications, they are unsuited for certain plant species and, further, are believed to provide lower yield due to the indiscriminate manner in which the plants are divided (causing much damage). Moreover, problems of needing excess liquid to facilitate blending and difficulties with cleaning and sterilization of numerous components are present with such processes.

In view of the foregoing, there is a need to provide an automated proliferation system which divides plant tissue and distributes it in a uniform manner under aseptic conditions while minimizing the above noted problems with prior art systems.

SUMMARY OF THE INVENTION

In accordance with the present invention, an automated plant culture proliferation system is provided utilizing a pick and place actuator having a movable gripper unit which removably engages a die cutting block which forms a number of cells arranged in a two-dimensional array. When the die cutter block is forced into a tissue culture container containing plant tissue of appropriate maturity, cut plant tissue and medium is forced into the cells of the cutter, thus forming a number of plugs of material. The cutter is then lifted out of the container and indexed to a wipe and feed mechanism which removes excess plant tissue and culture medium adhering to the side surfaces of the cutter in an aseptic manner. Thereafter, the pick and place actuator is indexed to another work station where the material of a fraction of the total number of cells of the cutter block are ejected into a new container containing culture medium. Additional containers receive material from the remaining cells of the cutter block until they are emptied. The actuator and ejection system are controlled so that each of the new containers receive plugs of plant tissue distributed in a uniform manner. Since the system uses a cutter block for the purposes of cutting and holding the material for distribution, only a single component needs to be cleaned and sterilized.

Additional benefits and advantages of the present invention will become apparent to those skilled in the art to which this invention relates from the subsequent description of the preferred embodiments and the appended claims, taken in conjunction with the accompanying drawings.

BRIEF DESCRIPTION OF THE DRAWINGS

FIGS. 3 through 7 illustrate the configuration of the gripper head and die cutter and the manner in which they are engaged and actuated.

FIG. 9 is a bottom view of the die cutter block.

FIGS. 19 through 22 illustrate the die cutter laden with plant tissue culture being positioned within four separate growth containers where material is ejected from selected cells of the cutter.

DETAILED DESCRIPTION OF THE INVENTION

Figure 1:
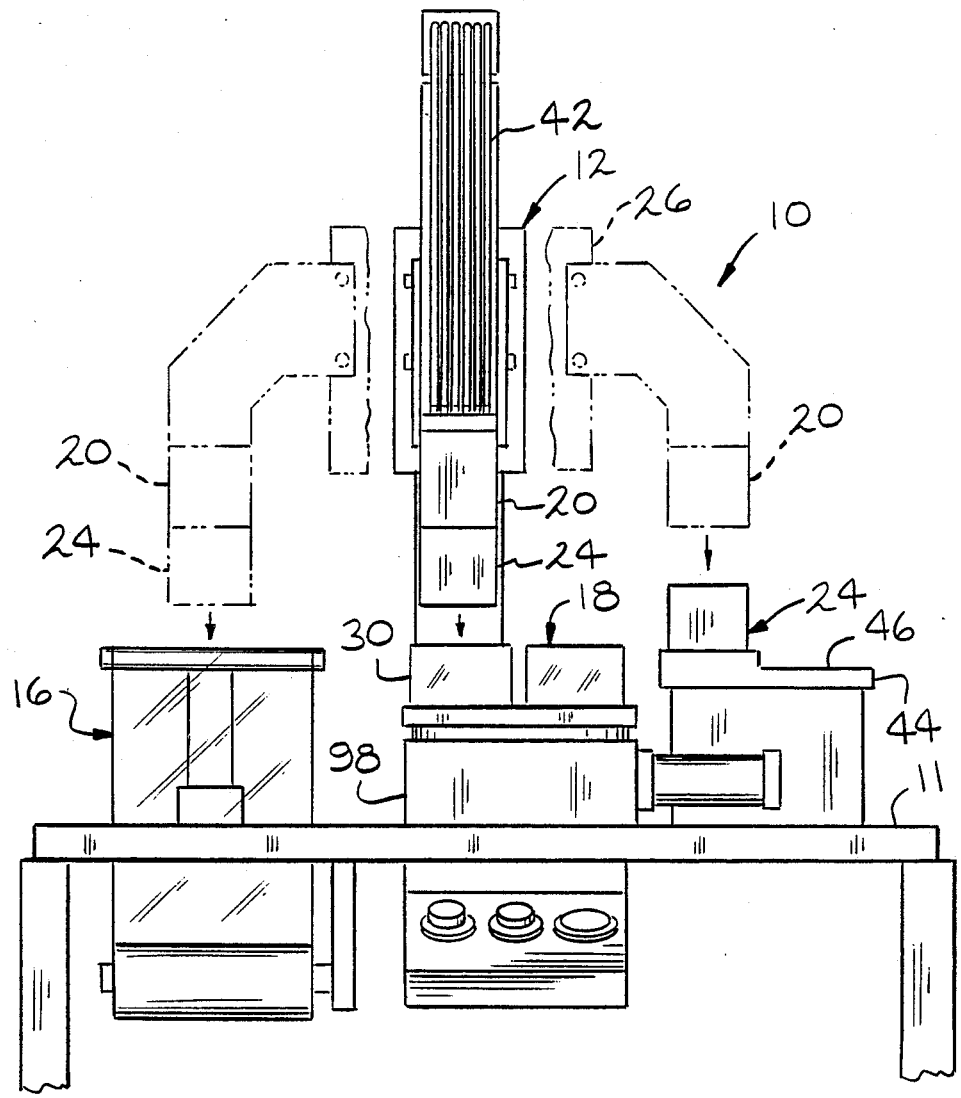
FIG. 1 is a pictorial side elevational view of an automated proliferation device in accordance with this invention showing the pick and place actuator with the three principal work stations of the device.
Figure 2:
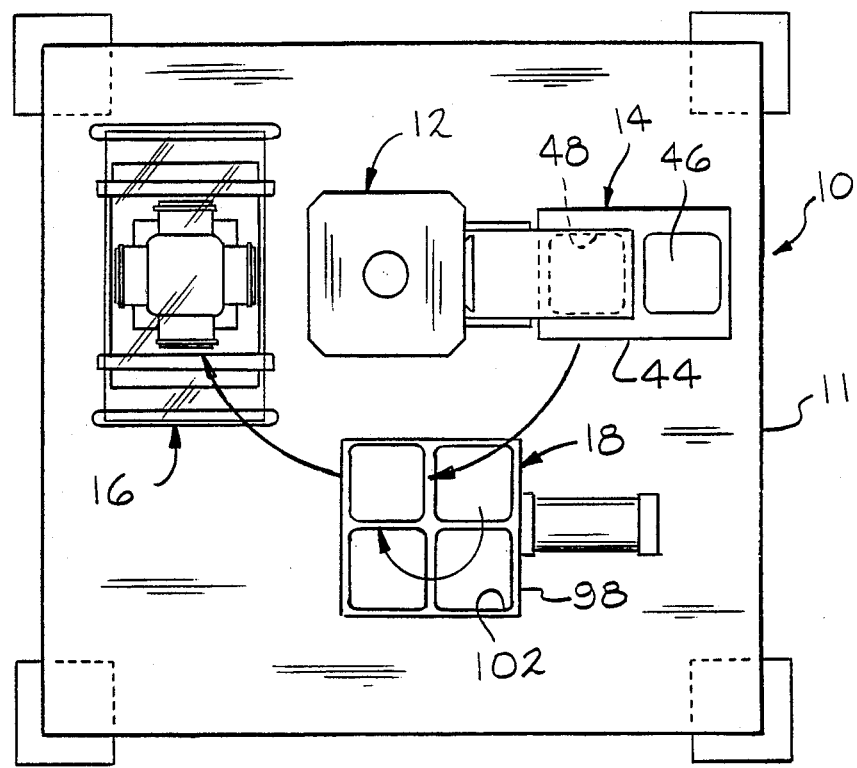
FIG. 2 is a top view of the device shown in FIG. 1.

A device for implementing the plant tissue culture proliferation system according to this invention, is shown in FIGS. 1 and 2, and is generally designated by reference number 10. Device 10 is supported by table 11 and principally comprises, a pick and place actuator 12 which has gripper head 20 that is movable into position at the pickup and cutting station 14, and a wipe and feed station 16, and a dispensing station 18. Pick and place actuator 12 rotates gripper head 20 about a vertical axis between the various work stations and also enables its vertical position to be controlled through vertical slide unit 26. Suitable control means, preferably of a programable type would be employed to control movement of actuator 12.

Now with reference to FIGS. 3 through 9, the configuration of gripper head 20 and the die cutter block 24 which it engages will be described. Gripper head 20 is adapted to provide a quick change capability for engaging cutter block 24. A number of pins designated by reference number 28 (four shown in the figures) are vertically movable through bores 30 within gripper head 20 and have elastomeric tips 32, preferably made of neoprene, at their ends. Each of pins 28 are connected to plate 34 and slide 36 of an air cylinder such that the pins can be actuated from the extended position shown in FIG. 3 to a retracted position where tips 32 are in engagement with the lower surface of gripper head 20. Cutter block 24 has blind bores 38 for accepting pins 28 which have a tapered section 39 defining an entrance bore diameter equal to the diameter of tips 32, as best shown in FIG. 7. Operation of the quick change mechanism is shown beginning at FIG. 3 where pins 28 are oriented in registry with bores 38, and thereafter the unit is displaced downwardly causing tips 32 to be received by the bores. Thereafter, slide 36 is actuated raising tips 38 and causing them to engage the lower surface of gripper 20. As shown in FIG. 7, compression of tips 32 causes them to expand radially, thus increasing their frictional engagement with the inside surfaces of bores 38, and thereby connecting cutter block 24 to gripper 20. FIG. 6 illustrates vertical slide unit 26 being actuated to lift cutter block 24. When the radial compression of tip 32 is relieved, a slight degree of frictional engagement between the tips and bores 38 is provided to retain cutter block 24 in place until an operator forceably removes it.

Figure 8:
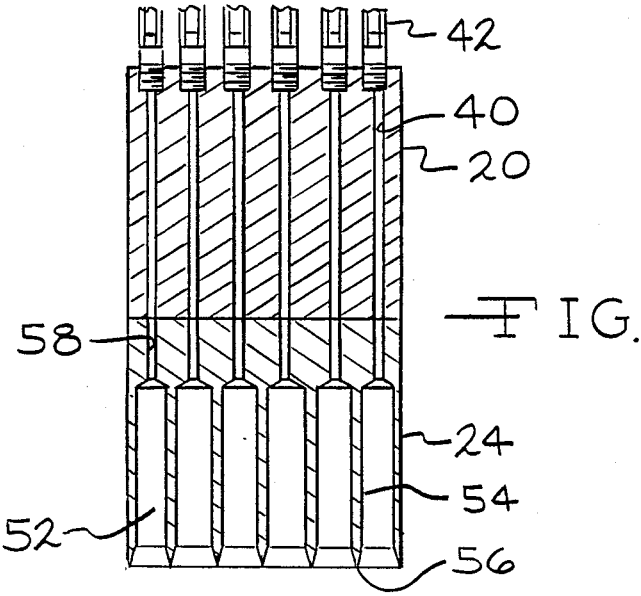
FIG. 8 is a cross-sectional view taken through the gripper head and die cutter block while they are in engagement.

Gripper head 20 includes a number of fluid passage bores 40 opening at its upper surface and connected to lines 42. The opposed ends of bores 40 open at the lower surface of the gripper head. Die cutter block 24 is machined to form a two-dimensional array of individual square shaped cells 52, as shown with reference to FIG. 9. In the example shown, a six-by-six array is provided, thus forming thirty-six individual cells 52. As will be apparent from the following description, other dimensions and shapes of arrays could be used. A thin wall 54 separates cells 52 and forms a sharpened knife edge lower surface 56. Fluid passage bores 58 communicate gripper bores 40 with each of cells 52. When gripper head 20 and cutter block 24 are connected as shown in FIG. 8, bores 40 and 58 are in registry enabling fluid pressure pulses (preferably air) applied through lines 42 to communicate with cells 52.

Figure 12:
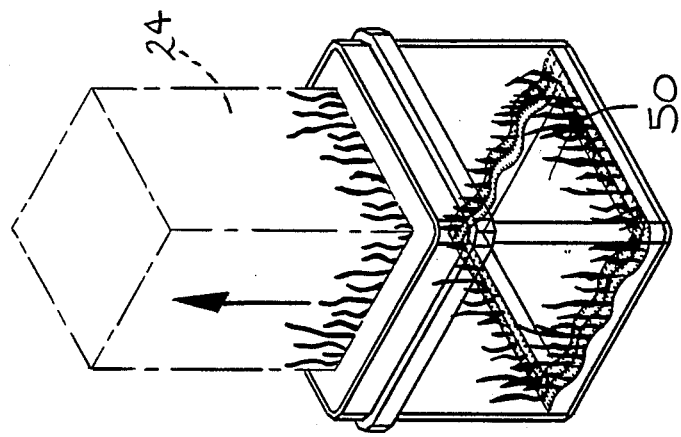
FIGS. 10 through 12 show the die cutter block being projected into a container containing plant tissue of appropriate maturity, cutting plant tissue and medium into a number of components and thereafter withdrawn.

The details of pickup and cutting station 14 are best explained by returning to FIGS. 1 and 2. Station 14 includes an indexible carrier 44 having a first machined pocket 46 for positioning and holding plant culture container 50, and a second machined pocket 48 for positioning and retaining cutter block 24. Container 50 is of conventional configuration (generally a square parallelopiped) and has an open top enclosed by a lid (not shown). During operation, indexible carrier 44 is moved to a position with gripper head 20 in registry with cutter block 24. Actuation of vertical slide unit 26 causes gripper 20 to engage cutter block 24, as previously explained. Vertical slide unit 26 is thereafter actuated to lift cutter block 24, and indexible carrier 44 is moved to position in registry with a container 50 containing plant medium with plant tissue of appropriate maturity. Vertical slide unit 26 is again actuated to force die cutter block 24 into container 50, as best shown with reference to FIGS. 10 through 12.

Figure 11:
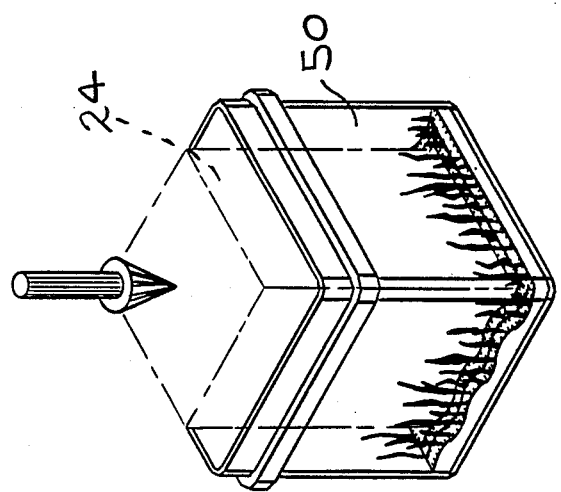
Figure 10:
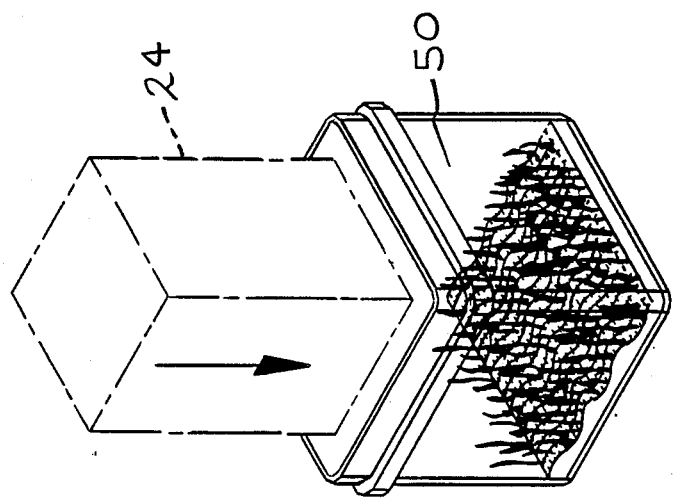

During the steps shown in FIGS. 10 and 11 in which cutter block 24 is stroked into container 50, the material within the container is cut into individual plugs within cells 52 in a die cutting or "cookie cutter" fashion. Friction and vicous forces maintain the individual plugs of cell tissue and medium within the cutter block cells 52. Container 50 at station 14 contains plant tissue arranged at nine principal plant sites arranged in a square three-by-three array (other arrangements are possible). As shown in FIG. 9, the plant site hearts or centers 60 are located such that they are each divided into four equal quadrants by cutter block 24. For reasons which will become apparent later in this description, it is necessary for cutter block 24 to be dimensioned to provide clearance around its side surfaces from the inside surfaces of container 50. Therefore, a perimeter ring of excess plant tissue and medium remains in the container after withdrawal of cutter 24. The existence of the excess material causes some to transfer to the cutter side surfaces.

After slide unit 26 is stroked vertically to pull cutter block 24 out of container 50, pick and place actuator 12 is rotated to move cutter block 24 into registry with wipe and feed station 16, best explained with reference to FIGS. 13 through 18. The functions of station 16 are to ensure separation of the culture plugs, to remove the material adhering to the side surfaces of cutter 24, and to carry away the excess tissue.

Figure 18:
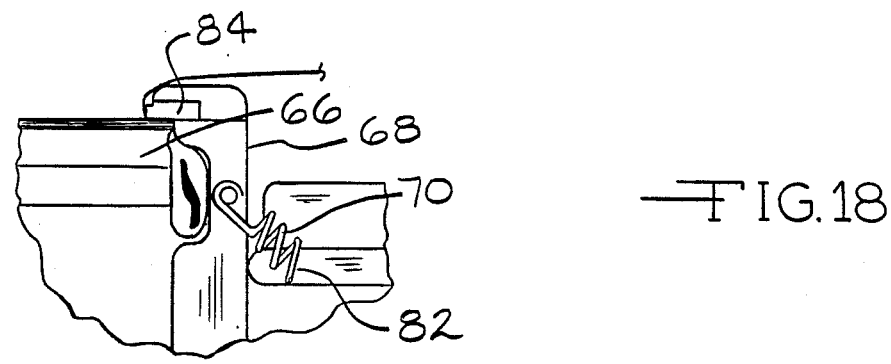

Wipe and feed station 16 is mounted to machine table 11 and includes an elevated platform or pad 66, preferably having a layer of elastic material such as urethane on its upper surface. On the four side surfaces of pad 66, articulated wiping arms 68 are provided which are pivotably mounted to carrier 76 and are normally biased into the position shown in FIGS. 13 through 15 by springs 70. A plastic membrane such as a Mylar sheet 78 is wrapped on drum 72 and passes over the top surface of pad 66 and is guided by rollers 74. In operation, cutter block 24 is pushed against pad 66 but is isolated from direct contact with the pad by Mylar sheet 78. Pick and place actuator 12 exerts a downward force slightly compressing pad 66 to insure that the plant medium and tissue is forced fully into cells 52 and separated. Cylinder 80 is thereafter actuated to pull carrier 76 downward. This action causes the outer surfaces of wiping arm 68 to engage risers 82 having cam surfaces, causing them to be actuated to rotate toward the side surfaces of cutter block 24. A wipe pad 84 carried by each arm 68 contacts sheet 78 and presses it against cutter 24. Continued downward motion of carrier 76 causes pads 84 to be drawn down the sides of cutter block 24, wiping them clean of excess material. Wipe pads 84 frictionally engage Mylar sheet 78, thus forming a pouch of trapped waste material as best shown in FIG. 18 as the wiping arms are drawn along the sides of the cutter block. Arms 68 are relieved to provide clearance for the trapped pouch. Thereafter, cutter block 24 is withdrawn from station 16 with its side surfaces virtually free of potentially contaminating tissue culture and medium.

Figure 13:
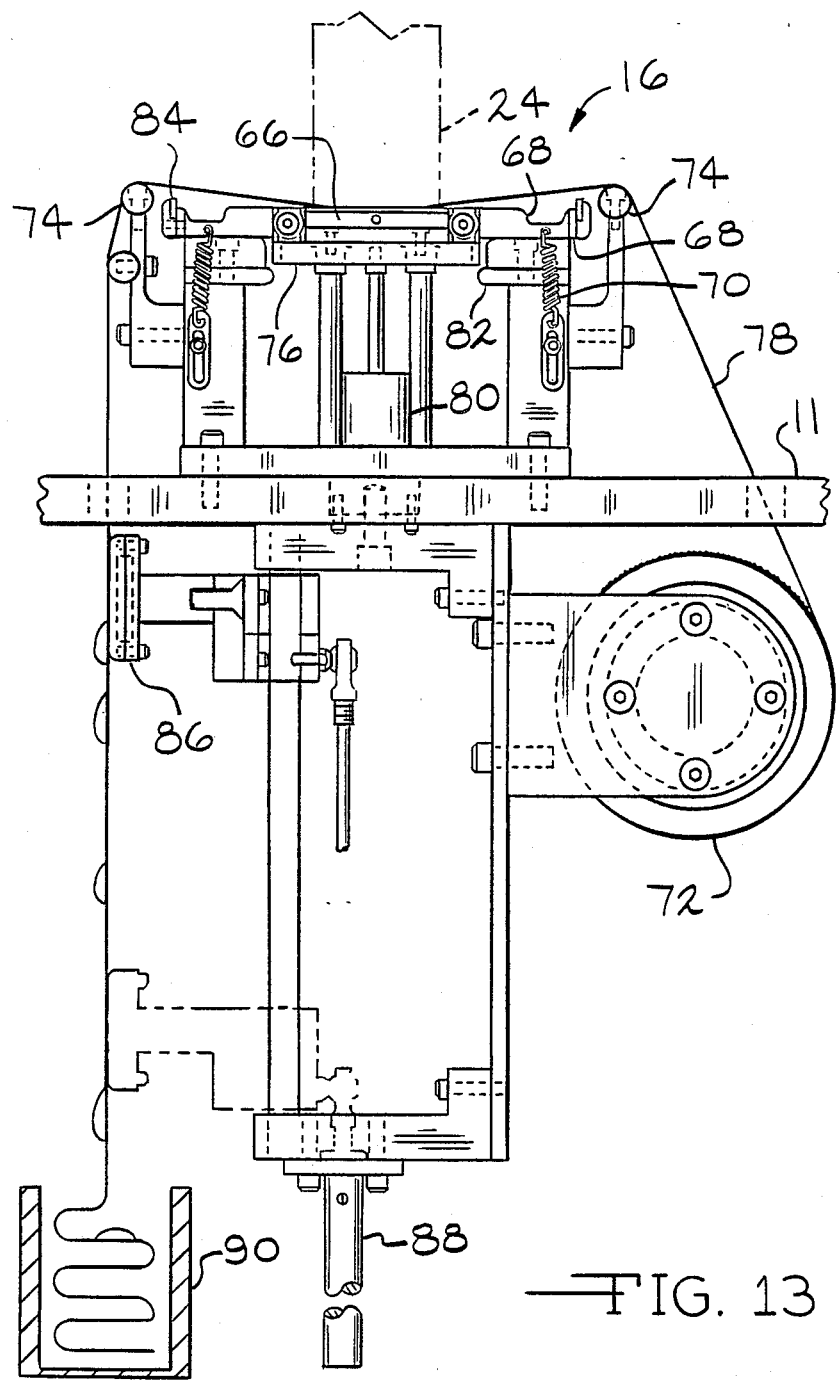
FIG. 13 is a side elevational view of the wipe and feed mechanism.
Figure 14:
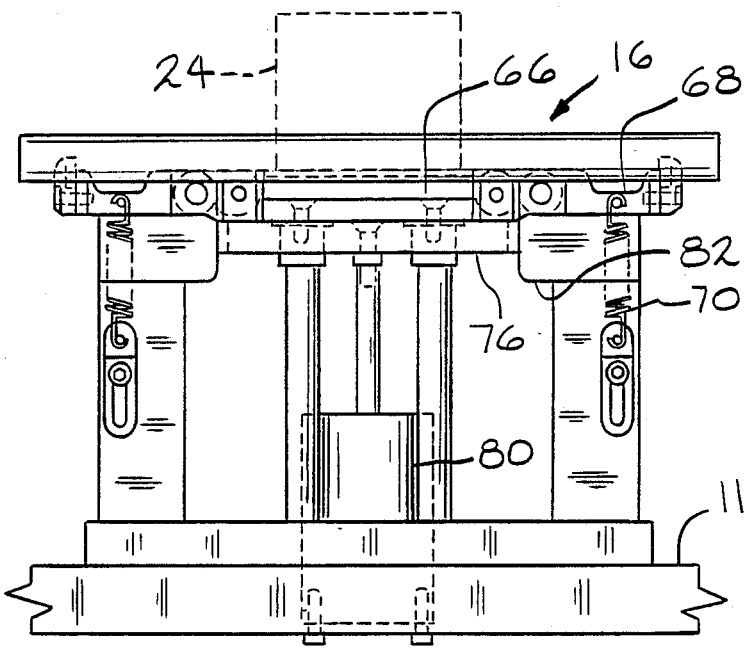
FIG. 14 is an enlarged side view of the mechanism shown in FIG. 13.
Figure 15:
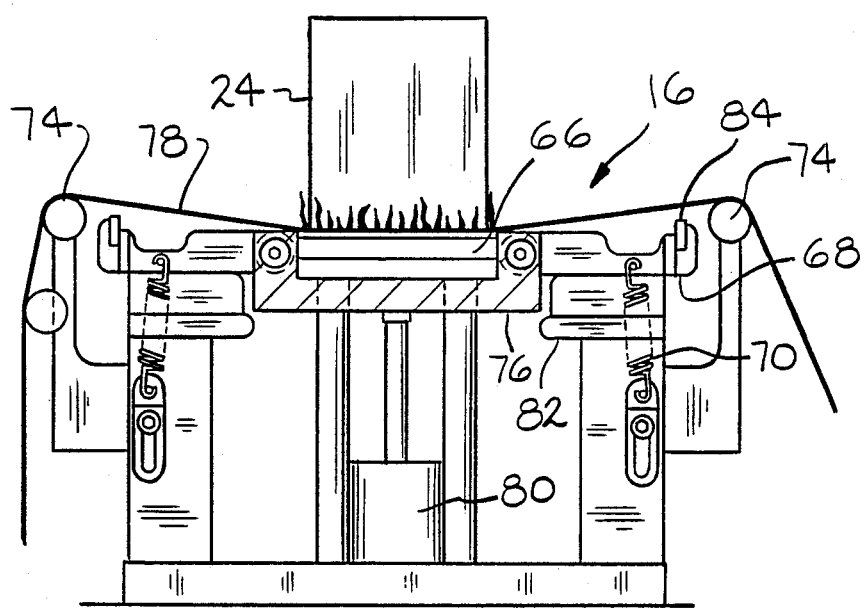
FIG. 15 is a partial front view of the wipe and feed mechanism shown in FIG. 14.
Figure 16:
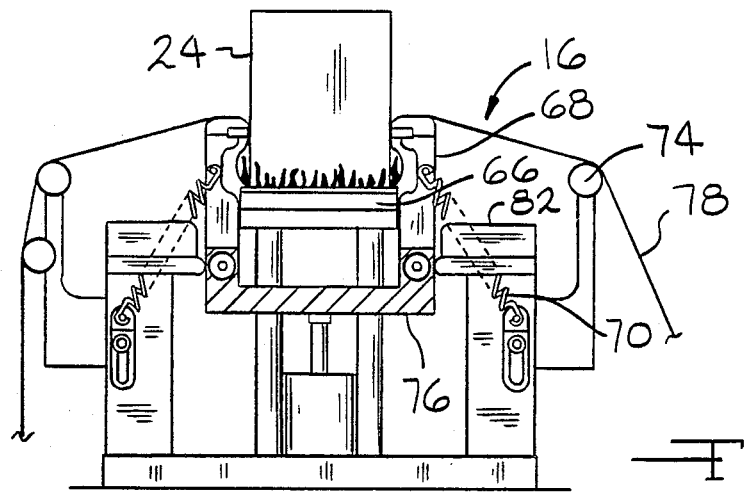
FIGS. 16 through 18 illustrate various positions for the wipe and feed mechanism showing excess material being removed from the outside surfaces of the die cutter block.
Figure 17:
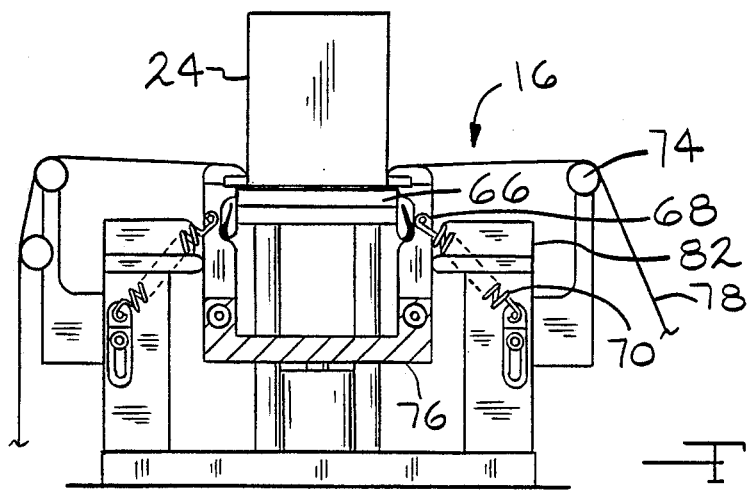

In order to insure sterility of cutter block 24 during the wiping operation, the surface of Mylar sheet 78 which engages cutter block 24 is continually renewed. With reference to FIG. 13, the indexing mechanism is shown and includes jaw 86 which engages Mylar sheet 78 and pulls it in a downward direction by actuation cylinder 88. The contaminated Mylar sheet is deposited within container 90 for disposal. Indexing of sheet 78 causes the excess material to be carried away since it has a gel like consistency making it stick to the sheet. By continually presenting a clean portion of Mylar sheet 78, the likelihood of contamination of the tissue culture within cutter block 24 is minimized.

The principles of isolating cutter block 24 from contamination of station 16 could also be employed at pickup and cutting station 14. An indexed plastic sheet interposed between cutter block 24 and carrier 44 would prevent the transference of contaminants between successive cutter blocks.

FIGS. 19 through 22 illustrate the unique positioning of cutter block 24 with respect to containers 50 set in each of the pockets 102 of the rotary turntable. As shown in FIG. 19, cutter block 24 is disposed in the lower left-hand corner of container 50 and nine individual cells 52 shown in shaded lines are caused to be ejected onto the tissue culture medium as shown in the figure. Each of the nine ejected pockets 48 is located in the upper right-hand quadrant of each of the plant heart centers 60 which originally cut at station 14. A blast of air through selected lines 42 is conducted into the appropriate gripper bores 30 and cells 52 to eject material from the shaded cells shown in FIG. 19. Cutter block 24 is thereafter withdrawn from one container 50 and turntable 98 is indexed to present a new container. For the next container, the position of cutter block 24 is displaced such that a different quadrant, in this case the lower right-hand quadrant of each heart center 60, is properly positioned with respect to the container and an appropriate air signal causes the tissue to be ejected from these cells 52. In similar fashion, two additional containers shown by FIGS. 21 and 22 are positioned relative to cutter block 24 so that, as the remaining quadrants are ejected, they are again deposited in a predetermined orientation with respect to containers 50. The result is that each container has an array of tissue plugs identically oriented at the positions shown in FIG. 9, i.e., centered with respect to the containers. This uniform placement of the ejected cell material plugs is desired since, after these plant cultures have matured sufficiently for division, cutter block 24 can be symmetrically positioned with respect to the container to again be located so that plant centers 60 can be cleaved into four generally equal quadrants.

Once each of containers 50 by carry rotary turntable 98 are planted, cutter block 24 is vertically withdrawn from the last container and is rotationally indexed 90 degrees to again be in registry with pickup and cutting station 14. While cutter block 24 is in its upward displaced position, an operator manually removes the used cutter block and loads a disinfected cutter block along with another container 50 with mature plants at that work station. In addition, the containers at rotary turntable 98 are removed and replaced with disinfected containers including only culture medium.

Apparatus 10 is preferably enclosed within a sealed compartment (not shown) to minimize the likelihood of contamination. The compartment would have access doors to permit intervention by an operator or robot when necessary.

Figure 23:
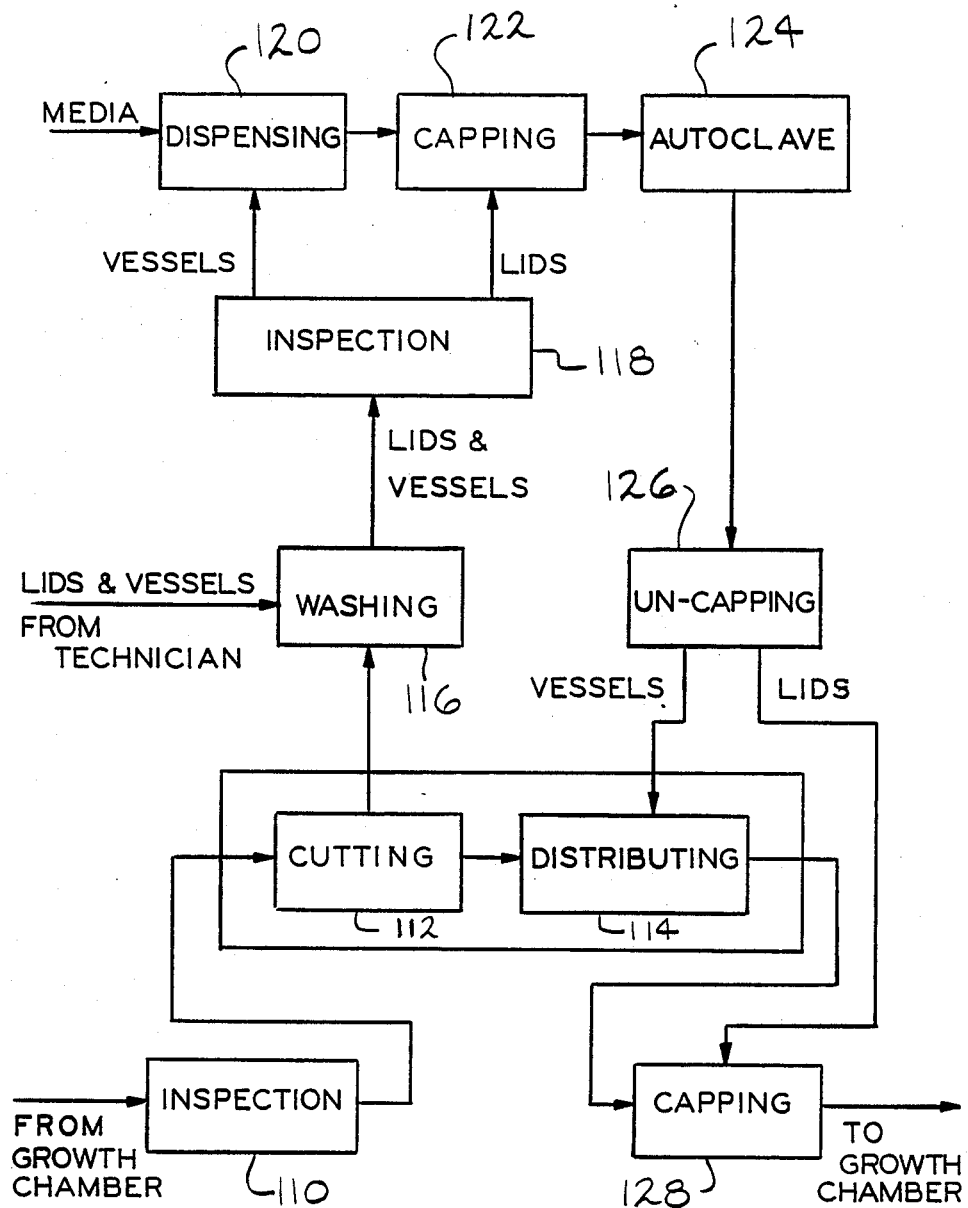
FIG. 23 is a flow chart showing the operational steps for the automated plant tissue culture proliferation system according to this invention.

Various steps of one process implementing the proliferation system in accordance with this invention are illustrated in block diagram form in FIG. 23. Block 110 is an inspection step at which a technician examines containers 50 taken from a growth chamber prior to loading them into apparatus 10 at pickup and cutting station 14. The cutting and distributing steps 112 and 114 are accomplished using apparatus 10 at work stations 14 and 18, as previously discussed. Following the cutting operation 112, containers 50 are sent to washing station 116 where remaining debris is removed. Additional containers 50 and lids can be added at station 116 as needed. Assuming that the containers and their lids pass inspection step 118, the containers are moved to dispensing station 120 where nutrient media is added. Thereafter, containers 50 are capped at station 122 and sent to autoclave 124 for disinfection. The disinfected containers and lids are then uncapped at station 126 and the containers are loaded at stations 14 and 18 and the lids are again added at capping station 128 after they receive tissue culture.

The processing of cutter block 24 begins with loading a disinfected block at station 14 prior to the cutting operation. After cutter 24 is recycled back to station 14, it is removed for cleaning. Preferably an element similar to gripper 20 would be used to engage cutter 24 and to blow a cleaning medium such as steam through each of cells 52. In addition, scrub brushes could be used to remove matter from the internal and external surfaces of the cutter block.

While the above description constitutes the preferred embodiments of the present invention, it will be appreciated that the invention is susceptible to modification, variation and change without departing from the proper scope and fair meaning of the accompanying claims.

What is claimed is:

1. An apparatus for automated plant tissue proliferation comprising:
    a first container containing plant tissue culture,
    a die cutter having a plurality of cells separated by walls defining cutting edges along a surface of said die cutter,
    means for indexing said die cutter into said first container and said culture thereby forcing said culture into said cells,
    a second container having culture medium, and
    ejection means for causing the material within a fraction of said cells to be ejected from said cells and deposited within said second container.

2. An apparatus according to claim 1 wherein said die cutter forms an array of rectangular cells and is oriented with respect to said first container so as to cut a plant center into four parts.

3. An apparatus according to claim 1 wherein said ejection means comprises forcing air into said cells causing the material within said cells to be expelled.

4. An apparatus according to claim 1 further comprising at least a third container for receiving material from a remaining fraction of said cells.

5. An apparatus according to claim 4 wherein said fraction of said cells ejected into said second container are distributed in an array arranged in a predetermined orientation with respect to said second container and said remaining fractions are distributed in said predetermined orientation.

6. An apparatus according to claim 1 further comprising a wiper mechanism for removing material from the outside surfaces of said die cutter after said cutter is indexed into said first container including at least one wiper arm articulated to engage said outside surfaces and moved along said surface and a membrane interposed between said cutter and said wiper arm to isolate said arm from said die cutter.

7. An apparatus according to claim 6 further comprising means for indexing said membrane to present a fresh surface of said membrane for wiping said die cutter.

8. An apparatus according to claim 1 wherein upon withdrawal of said die cutter, said culture is retained within said cells through viscous and frictional forces.

9. An apparatus for plant tissue proliferation comprising:
   a first container containing plant tissue culture,
   a die cutter having a plurality of cells separated by walls defining cutting edges,
   indexing means having a gripper for releasably holding said die cutter and vertically indexing said die cutter causing said die cutter to be forced into said first container and into said culture forcing said culture into said cells and thereby differentiating said plant tissue culture,
   a second container containing plant tissue culture medium, and
   passages communicating with said cells and means for applying fluid pressure to a preselected fraction of said cells for causing material from said fraction to be ejected into said second container.

10. An apparatus according to claim 9 wherein said die cutter forms an array of rectangular cells and is oriented with respect to said first container so as to cut a plant center into four parts.

11. An apparatus according to claim 9 further comprising at least a third container for receiving material from a remaining fraction of said cells.

12. An apparatus according to claim 11 wherein said fraction of said cells ejected into said second container are distributed in an array arranged in a predetermined orientation with respect to said second container and said remaining fractions are distributed in said predetermined orientation.

13. An apparatus according to claim 9 further comprising a wiper mechanism for removing material from the outside surfaces of said die cutter after said cutter is indexed into said first container including at least one wiper arm articulated to engage said outside surface and move along said surface and a membrane interposed between said cutter and said wiper arm to isolate said arm from said die cutter.

14. An apparatus according to claim 13 further comprising means for indexing said membrane to present a fresh surface of said membrane for wiping said die cutter.

15. An apparatus according to claim 9 wherein upon withdrawal of said die cutter said culture is retained within said cells through viscous and frictional forces.

16. An apparatus according to claim 9 wherein said gripper defines a plurality of fluid passages which are positioned to communicate with fluid passages in said die cutter when said gripper is engaging said die cutter.

17. An apparatus according to claim 16 further comprising quick connection means for connecting said gripper to said die cutter including at least one retractable pin carried by said gripper having an elastomeric tip which is received by a bore in said die cutter and actuation means compressing said tip causing said tip to expand thereby frictionally engaging said cutter bore.

18. An apparatus for plant tissue proliferation comprising:
   a pick and place actuator having an arm indexible vertically and rotatable about a vertical axis to a plurality of work stations positions,
   a die cutter defining a plurality of cells separated by walls defining cutting edges and having fluid passages communicating with said cells,
   a gripper carried by said actuator arm for removably engaging said die cutter and having fluid passages communicating with said die cutter passages when said gripper engages said die cutter,
   a cutting station for positioning a first container containing culture medium such that vertical indexing of said die cutter forces said cutter into said first container forcing said culture into said cells,
   a wiping station for removing material from the outside surfaces of said die cutter including at least one wiping arm with articulation means for moving said arm into engagement with said side surfaces and moving down said surfaces, and a membrane interposed between said wiper arm and said surface to isolate said side surface from said arm,
   ejection means for providing a fluid pulse through said gripper and die cutter passages thereby dispensing material from said die cutter cells, and
   a dispensing station having at least second and third containers containing culture medium, wherein said actuator orients said die cutter with respect to said second container and said ejection means operable to eject material from a fraction of said cells to produce an array in said second container having a predetermined configuration and orientation with respect to said second vessel and said die cutter and said ejection means operated to eject material from a remaining fraction of said cells to produce an array in said third container of said predetermined configuration and orientation with respect to said third container.

19. An apparatus according to claim 18 wherein said die cutter forms an array of rectangular cells and is oriented with respect to said first container so as to cut a plant center into four parts.

20. An apparatus according to claim 18 wherein said wiper mechanism further comprises indexing means for presenting a fresh surface of said membrane for contact with said die cutter.

21. An apparatus according to claim 18 wherein upon withdrawal of said die cutter said culture is retained within said cells through viscous and frictional forces.

22. An apparatus according to claim 18 further comprising quick connection means for connecting said gripper to said die cutter including at least one retractable pin carried by said gripper having an elastomeric tip which is received by a bore in said die cutter and actuation means for compressing said tip causing said tip to expand radially thereby frictionally engaging said cutter bore.

23. A gripper for removably engaging a die cutter forming a number of cells for a plant tissue proliferation system comprising:
   a body defining a bottom surface with a plurality of fluid passages therein,
   mounting means for connection with said die cutter to support said die cutter against said bottom surface such that said gripper passages communicate with passages in said cutter communicating with said cells, and
   fluid pressure generating means communicating with said gripper passages such that plant material and culture medium within said die cutter cells can be ejected therefrom by fluid pressure.

24. A gripper according to claim 23 wherein said mounting means comprises at least one pin projecting from said gripper bottom surface and having an elastomeric tip and actuation means for moving said tip between a projected position to a retracted position compressing said tip against said gripper bottom surface, and said die cutter having bores for receiving said tip whereby said retraction of said tip causes said tip to expand radially thereby frictionally engaging said die cutter.

25. A wiper mechanism for removing material from outside surfaces of a die cutter having a plurality of cells for cutting plant tissue and culture medium for use in a plant tissue proliferation system comprising:
a platform for engaging the surface of said cutter divided into said cells,
at least one articulated arm,
actuation means for moving said arm to engage said outside surfaces of said cutter and wipe along said surfaces toward said divided surface, and
a membrane disposed between said die cutter and said platform and arm for isolating said cutter from contamination.

26. A wiper mechanism according to claim 25 further comprising an elastomeric wiping tip engaging said membrane to pull said membrane along said outside surfaces.

27. A wiper mechanism according to claim 25 further comprising means for indexing said membrane to present a fresh surface of said membrane for wiping said die cutter.

28. A method of plant tissue culture propogation comprising the steps of:
providing a first container having plant tissue culture therein,
providing a die cutter defining a plurality of divided cells,
forcing said die cutter into said first container and into said plant tissue culture thereby dividing said tissue culture as said tissue culture is forced into said cells,
providing a second container having plant culture mediums, and
ejecting material from a fraction of said said cells into said second container.

29. A method of plant tissue culture propagation according to claim 28 further comprising the step of wiping off side surfaces of said die cutter after forcing said die cutter into said first container.

30. A method of plant tissue culture propagation according to claim 28 wherein said first container contains plant tissue culture defining a plurality of individual plant centers and wherein said die cutter divides said centers into a number of parts.

* * * * *